(12) United States Patent
Dedent et al.

(10) Patent No.: US 10,954,572 B2
(45) Date of Patent: Mar. 23, 2021

(54) **POLYNUCLEOTIDES FOR THE AMPLIFICATION AND DETECTION OF *NEISSERIA GONORRHOEAE***

(71) Applicant: Talis Biomedical Corporation, Menlo Park, CA (US)

(72) Inventors: Andrea C. Dedent, San Francisco, CA (US); Hedia Maamar, El Dorado Hills, CA (US); Dana Kelly Vanatta, San Mateo, CA (US)

(73) Assignee: Talis Biomedical Corporation, Menlo Park, CA (US)

( * ) Notice: Subject to any disclaimer, the term of this patent is extended or adjusted under 35 U.S.C. 154(b) by 0 days.

(21) Appl. No.: 16/719,744

(22) Filed: Dec. 18, 2019

(65) Prior Publication Data

US 2021/0024980 A1   Jan. 28, 2021

Related U.S. Application Data

(63) Continuation of application No. 16/523,609, filed on Jul. 26, 2019.

(60) Provisional application No. 62/878,639, filed on Jul. 25, 2019.

(51) Int. Cl.
*C12Q 1/689* (2018.01)

(52) U.S. Cl.
CPC ........ *C12Q 1/689* (2013.01); *C12Q 2600/112* (2013.01); *C12Q 2600/16* (2013.01); *C12Q 2600/166* (2013.01)

(58) Field of Classification Search
None
See application file for complete search history.

(56) References Cited

U.S. PATENT DOCUMENTS

| | | | |
|---|---|---|---|
| 5,155,018 A | 10/1992 | Gillespie et al. | |
| 5,234,809 A | 8/1993 | Boom et al. | |
| 5,512,445 A | 4/1996 | Yang et al. | |
| 6,001,611 A | 12/1999 | Will | |
| 6,383,393 B1 | 5/2002 | Colpan et al. | |
| 7,728,119 B2 | 6/2010 | Nakamura et al. | |
| 9,187,789 B2 | 11/2015 | Pabich et al. | |
| 9,434,999 B1 | 9/2016 | Ao et al. | |
| 9,982,312 B2 | 5/2018 | Pearce et al. | |
| 2008/0276335 A1 | 11/2008 | Abad et al. | |
| 2008/0299567 A1 | 12/2008 | Marshall et al. | |
| 2012/0100551 A1 | 4/2012 | Kojima et al. | |
| 2013/0017539 A1 | 1/2013 | Singhal et al. | |
| 2013/0265054 A1 | 10/2013 | Lowery, Jr. et al. | |
| 2014/0308663 A1 | 10/2014 | Yonekawa et al. | |
| 2015/0159205 A1 | 6/2015 | Narayanan et al. | |
| 2015/0267266 A1 | 9/2015 | Soetaert et al. | |
| 2015/0322493 A1 | 11/2015 | Tulp et al. | |
| 2016/0257998 A1 | 9/2016 | Persing et al. | |
| 2016/0273029 A1* | 9/2016 | Suwara | C12Q 1/6825 |
| 2016/0319378 A1 | 11/2016 | Rey | |
| 2019/0111423 A1* | 4/2019 | Ismagilov | B01L 3/50273 |
| 2019/0284617 A1 | 9/2019 | Lee et al. | |
| 2019/0284618 A1 | 9/2019 | Dedent et al. | |
| 2019/0345541 A1 | 11/2019 | Dedent et al. | |
| 2020/0002752 A1 | 1/2020 | Dedent et al. | |

FOREIGN PATENT DOCUMENTS

| | | |
|---|---|---|
| CN | 101831488 A | 9/2010 |
| CN | 101886122 A | 11/2010 |
| CN | 107099618 A | 8/2017 |
| EP | 2787077 A1 | 10/2014 |
| WO | 2011/144304 A1 | 11/2011 |
| WO | 2015/058008 A1 | 4/2015 |
| WO | 2015/063498 A2 | 5/2015 |
| WO | 2016/011280 A1 | 1/2016 |
| WO | 2016/085632 A2 | 6/2016 |
| WO | 2016105508 A2 | 6/2016 |
| WO | 2017/192902 A1 | 11/2017 |
| WO | 2018/089942 A8 | 5/2018 |
| WO | 2018/089943 A1 | 5/2018 |
| WO | 2018/089945 A8 | 5/2018 |
| WO | 2019/217627 A1 | 11/2019 |

OTHER PUBLICATIONS

Jevtuševskaja, J. et al., "Combination with antimicrobial peptide lyses improves loop-mediated isothermal amplification based method for *Chlamydia trachomatis* detection directly in urine sample," BMC Infectious Diseases, (2016) 16:329.

Liu, M., et al., "Loop-mediated isothermal amplification of *Neisseria gonorrhoeae* porA pseudogene: a rapid and reliable method to detect gonorrhea," AMB Express, (2017) 7:48.

International Written Opinion of the International Searching Authority for PCT/US2017/061402, dated Apr. 18, 2018, 8 pages.

Xu, G. et al., "A capillary-based multiplexed isothermal nucleic acid-based test for sexually transmitted diseases in patients", Chemical Communications, vol. 52, No. 82, Sep. 8, 2016, pp. 12187-12190, XP055483578.

Supplemental Partial European Search Report for EP 17868914, dated Apr. 22, 2020, 15 pages.

Edwards, T. et al., "Loop-Mediated Isothermal Amplification Test for Detection of Neisseria gonorrhoeae in Urine Samples and Tolerance of the Assay to the Presence of Urea", Journal of Clinical Microbiology, Mar. 12, 2014, vol. 52, No. 6, pp. 2163-2165, entire document.

(Continued)

*Primary Examiner* — Samuel C Woolwine
(74) *Attorney, Agent, or Firm* — Goodwin Procter LLP

(57) ABSTRACT

Disclosed herein are primers and probes related to the detection of *Neisseria gonorrhoeae* via nucleic acid amplification testing (NAAT), for example to amplify and determine the presence of *N. gonorrhoeae* nucleic acids present in test samples. Specifically the present disclosure describes primers and probes that bind to Cytochrome C or ccpA gene of *N. gonorrhoeae* for detection via loop mediated isothermal amplification (LAMP) and molecular beacon hybridization.

27 Claims, No Drawings
Specification includes a Sequence Listing.

(56) References Cited

OTHER PUBLICATIONS

International Search Report and the Written Opinion of the International Searching Authority for PCT/US2017/061405, dated Apr. 20, 2018, 18 pages.
International Search Report and the Written Opinion for PCT/US2017/061403, dated Feb. 13, 2018, 16 pages.
Choopara, I., et al, "Rapid and visual Chlamydia trachomatls detection using loop-mediated Isothermal amplification and hydroxynaphthol blue" Letters in Applied Microbiology, Sep. 30, 2016, vol. 64, Iss. 1, pp. 51-56.
Choopara, I., et al., "Development of Chlamydia trachomatis detection by loop-mediated isothermal amplification," International Journal of Biomedical Science & Bioinformatics, 2015, vol. 2, Issue 1, pp. 21-25.
Little, M., et al. "Strand Displacement Amplification and Homogeneous Real-Time Detection Incorporated in a Second-Generation DNA Probe System, BDProbeTecET." Clinical Chemistry, 1999, vol. 45, No. 6, pp. 777-784.
Ng, L-K., et al., "The laboratory diagnosis of Neisseria gonorrhoeae," Can J Infect Dis Med Microbiol., 2005, vol. 16, No. 1, pp. 15-25.
Njiru, Z., "Loop-Mediated Isothermal Amplification Technology: Towards Point of Care Diagnostics." PLoS Negl Trop Dis., 2015, vol. 6, No. 6, e1572, pp. 1-4.
Nixon, G., et al., "A novel approach for evaluating the performance of real time quantitative loop-mediated isothermal amplification-based methods." Biomolecular Detection and Quantification, 2014, vol. 2, pp. 4-10.
Xu, G., et al. "Rapid ultrasonic isothermal amplification of DNA with multiplexed melting analysis—applications in the clinical diagnosis of sexually transmitted diseases." Chem. Commun., 2015, vol. 51, pp. 2589-2592.
Yamamoto, R., et al., "Molecular beacon aptamer fluoresces in the presence of Tat protein of HIV-1," Genes to Cells, 2000, vol. 5, pp. 389-396.
Zanoli, L. et al., "Isothermal Amplification Methods for the Detection of Nucleic Acids in Microfluidic Devices." Biosensors, 2013, vol. 3, pp. 18-43.
International Search Report and the Written Opinion of PCT/US19/31439, dated Sep. 13, 2019, 18 pages.
Bakheit, et al. "Sensitive and specific detection of *Cryptosporidium* species in PCR-negative samples by loop-mediated isothermal DNA amplification and confirmation of generated LAMP products by sequencing." Vetrin. Parasitology 158:11-22 (2008).
Fan, et al. "The Development and Evaluation of a Loop-Mediated Isothermal Amplification Method for the Rapid Detection of *Salmonella enterica* serovar Typhi." PLoS ONE 10(4): e0124507. (2015) doi:10.1371/journal.pone.0124507.
Gandelman, et al. "Loop-Mediated Amplification Accelerated by Stem Primers." Int. J. Mol. Sci. 12:9108-9124 (2011).
Iwamoto, et al. "Loop-Mediated Isothermal Amplification for Direct Detection of *Mycobacterium tuberculosis* Complex, *M. avium*, and M. intracellulare in Sputum Samples." J. Clin Microbiol. 41(6):2616-2622 (2003).
Lee, et al. "Clinical Evaluation of a Loop-Mediated Isothermal Amplification (LAMP) Assay for Rapid Detection of Neisseria meningitidis in Cerebrospinal Fluid." PLoS ONE 10(4): e0122922. (2015) doi:10.1371/journal.pone.0122922.
Liu, et al. "Establishment of an accurate and fast detection method using molecular beacons in loop-mediated Isothermal amplification assay." Scientific Reports 7:40125 (Jan. 2017). DOI:10.1038/srep40125.
Nagamine, et al. "Accelerated reaction by loop-mediated isothermal amplification using loop primers." Mol. Cell. Probes 16:223-229 (2002).
Tanner, et al. Simultaneous multiple target detection in real-time loop-mediated isothermal amplification, Biotechniques 2012, 53, 81-89.
Wang, et al. "Rapid and Sensitive Detection of *Shigella* spp. and *Salmonella* spp. By Multiple Endonuclease Restriction Real-Time Loop-Mediated Isothermal Amplification Technique." Frontiers Microbiol. 6:1400. (2015). doi:10.3389/fmicb.2015.01400.
Wang, et al. "Two Methods for Increased Specificity and Sensitivity in Loop-Mediated Isothermal Amplification." Molecules 20:6048-6059 (2015). doi:10.3390/molecules20046048.
WHO Expert Group Meeting Report. "The Use of Commercial Loop-Mediated Isothermal Amplification Assay (TB-LAMP) for the Detection of Tuberculosis." May 2013.
Wong, et al. "Loop-mediated isothermal amplification (LAMP): a versatile technique for detection of micro-organisms." J. Appl. Microbiol. 124:626-643 (2017).
Yamakura, et al. "Evaluation of a New Rapid Molecular Diagnostic System for Plasmodium falciparum Combined with DNA Filter Paper, Loop-Mediated Isothermal Amplification, and Melting Curve Analysis." Jpn. J. Infect. Dis. 62:20-25 (2009).
Neejara, M., et al: "Rapid detection and differentiation of dengue virus serotypes by NSI specific reverse transcription loop-mediated isothermal amplification (RT-LAMP) assay in patients presenting to a tertiary care hospital in Hyderabad, India", Journal of Virological Methods, vol. 211, Jan. 1, 2015 (Jan. 1, 2015), pp. 22-31, XP055706867, NL ISSN: 0166-0934, DOI: 10.1016/j.jviromet.2014.10.005.
Broude N., "Stem-loop obligonucleotides: a robust tool for molecular biology and biotechnology", IN Biotechnology, Elsevier Publications, Cambridge, GB, vol. 20, No. 6, Jun. 1, 2002 (Jun. 1, 2002), pp. 249-256, XP004352763, ISSN: 0167-7799, DOI: 10.1016/S0167-7799(02)01942-X.
European Supplementary Partial European Search Report for Application EP 17 86 9399, dated Jul. 3, 2020, 16 pages.

\* cited by examiner

SEQUENCE LISTING

```
<160> NUMBER OF SEQ ID NOS: 76

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cataaggaat acacgatgtc tttc                                             24

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 2
gattttctgc atttcttcga ca                                            22

<210> SEQ ID NO 3
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
aagcaggaga agcatcgcct attggcattg tcttcactgt                          40

<210> SEQ ID NO 4
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cgcccgaaga ccaagaccgt cggcaaaggt tggaata                             37

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gccgcagact tttcctga                                                  18

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tttgaaacgc gcgcaag                                                   17

<210> SEQ ID NO 7
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
aaggcaacgt caacgc                                                    16

<210> SEQ ID NO 8
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
```
gtcagcacgg cctttg         16

<210> SEQ ID NO 9
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
caccgttgtg gcaggcactg agcgaacagg aacg         34

<210> SEQ ID NO 10
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
caaccttgga ggcacgacct gaatttccaa tacggccc         38

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gttgtccatg aacgcgc         17

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cagaaattcg gtctggtcca         20

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tattccaacc tttgccgac         19

<210> SEQ ID NO 14
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14

```
gccgaactgc cctttg                                                          16

<210> SEQ ID NO 15
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ctttggaaag gcgtggttca tacccgttta ccgaagaaca gg                              42

<210> SEQ ID NO 16
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
caaaggcaat accgtaagct gccatattgt ccacaccggc                                40

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cagagttggt gtccgagtt                                                       19

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cttgccacaa ccttgcttc                                                       19

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tatttccaca acggcagc                                                        18

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ggcttagatt ccatcggtg                                                       19
```

<210> SEQ ID NO 21
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ccacatcttc tttcggaatg tcttttggga gctggataag gc                          42

<210> SEQ ID NO 22
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gtggataaca tcgtcgtatt cctgacagtt ccggcatcgt g                           41

<210> SEQ ID NO 23
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
caattgcgcc ttacccatg                                                    19

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ctttccggca atgtttccg                                                    19

<210> SEQ ID NO 25
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ttgtcgcgtt tcggatc                                                      17

<210> SEQ ID NO 26
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ccaacctttg ccgactg                                                      17

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
catcactacc gcattggg                                                 18

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cagaccgaat ttctggaagg                                               20

<210> SEQ ID NO 29
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gctcagggcg ttgacgtgtt tgagcgtacc ctgc                               34

<210> SEQ ID NO 30
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gcgcgttcat ggacaacgcg tgcctccaag gttg                               34

<210> SEQ ID NO 31
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ccatttggtc ggcgtca                                                  17

<210> SEQ ID NO 32
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gctgtattgc ctgccaca                                                 18

<210> SEQ ID NO 33
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
cttagattcc atcggtgcg                                                      19

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ggcaatgttt ccgaatcagc                                                     20

<210> SEQ ID NO 35
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gcgatgcttc tcctgc                                                         16

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gtgtccgagt ttgacctg                                                       18

<210> SEQ ID NO 37
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gaagcggaag gaacggcttt tccgagaccg aagcg                                    35

<210> SEQ ID NO 38
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ctcgcccgaa gaccaagact ctgcatttct tcgacagtc                                39

<210> SEQ ID NO 39

```
<210> SEQ ID NO 39
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ggcctgtact tgggaagc                                                       18

<210> SEQ ID NO 40
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gcgcaaggtg tattccaac                                                      19

<210> SEQ ID NO 41
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gtgtccgagt ttgacctgt                                                      19

<210> SEQ ID NO 42
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
caaccttgct tccgcc                                                         16

<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
tcattcgcca tttccacc                                                       18

<210> SEQ ID NO 44
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
atgcggtagg cgagttgcgt ggacaatatg ccgacc                                   36

<210> SEQ ID NO 45
<211> LENGTH: 35
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gggcagccag ttttgggaga ttcaccaaag gcccg                               35

<210> SEQ ID NO 46
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ccctttgtgc ccctgac                                                   17

<210> SEQ ID NO 47
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
gtgccgccga tgttga                                                    16

<210> SEQ ID NO 48
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
aactcggaca ccaactc                                                   17

<210> SEQ ID NO 49
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
cattcaatgc ggtaggc                                                   17

<210> SEQ ID NO 50
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
agcaaggttg tggcaagagg gtatgaacca cgcctt                              36

<210> SEQ ID NO 51
<211> LENGTH: 32
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 51
cgccggtgtg gacaatgaac tgccctttgt gc                                 32

<210> SEQ ID NO 52
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
cagcttacgg tattgcctt                                                19

<210> SEQ ID NO 53
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
atgccgacca gtcagg                                                   16

<210> SEQ ID NO 54
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
atatgccgac cagtcag                                                  17

<210> SEQ ID NO 55
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
gggaactttg gcgattt                                                  17

<210> SEQ ID NO 56
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
agcagcgcag cattcaatgc acaaagggca gttc                               34

<210> SEQ ID NO 57
<211> LENGTH: 36
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 57
tgttgaagaa caggctggcg cgaatcattc gccatt                               36

<210> SEQ ID NO 58
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
gtaggcgagt tgcgtc                                                     16

<210> SEQ ID NO 59
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
ttggtgaatc cggtgga                                                    17

<210> SEQ ID NO 60
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
gagttgcgtc cgccgaactg cctcttgcca caaccttgct tccg                      44

<210> SEQ ID NO 61
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
accgcattga atgctgcgct gctgcccgcc agcctgttct tc                        42

<210> SEQ ID NO 62
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
tgactggtcg gcatattgtc cacac                                           25

<210> SEQ ID NO 63
<211> LENGTH: 19
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 63
cggacgtgcc gccgatgtt                                                19

<210> SEQ ID NO 64
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
cctttccaaa ggcaataccg taagc                                         25

<210> SEQ ID NO 65
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
tcgccatttc caccggattc ac                                            22

<210> SEQ ID NO 66
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
tgcggtaggc gagttgcggg acaatatgcc gaccagt                            37

<210> SEQ ID NO 67
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
ttgaatgctg cgctgctggc agcctgttct tcaacatcg                          39

<210> SEQ ID NO 68
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
cgaactgccc tttgtgcc                                                 18

<210> SEQ ID NO 69
<211> LENGTH: 16
<212> TYPE: DNA
<213> ORGANISM: Artificial Sequence
<220> FEATURE:
<223> OTHER INFORMATION: Description of Artificial Sequence: Synthetic primer

<400> SEQUENCE: 69
ttgggacgga cgtgcc                                                                16

<210> SEQ ID NO 70
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
tgccacaacc ttgcttcc                                                              18

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
cgaatcattc gccatttcca                                                            20

<210> SEQ ID NO 72
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
ctttggaaag gcgtggttca tacaaatccg tccgtttacc g                                    41

<210> SEQ ID NO 73
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 73
ccgcaacgtg ccgccgatgt tgcgg                                                      25

<210> SEQ ID NO 74
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 74
gcgtgacgga cgtgccgccg atgtcacgc                                                  29

<210> SEQ ID NO 75
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 75
cgttgggacg gacgtgccgc caacg                                          25

<210> SEQ ID NO 76
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 76
cggggacgga cgtgccgccg atgtccccg                                      29
```

POLYNUCLEOTIDES FOR THE AMPLIFICATION AND DETECTION OF *NEISSERIA GONORRHOEAE*

CROSS-REFERENCE TO RELATED APPLICATIONS

This application is a continuation of U.S. patent application Ser. No. 16/523,609, filed Jul. 26, 2019, which claims the benefit of U.S. Provisional Application No. 62/878,639, filed Jul. 25, 2019, the contents of which are each incorporated by reference in their entirety.

SEQUENCE LISTING

The instant application contains a Sequence Listing which has been filed electronically in ASCII format and is hereby incorporated by reference in its entirety. Said ASCII copy, created on Dec. 18, 2019, is named TSM-052C1 SL.txt and is 17,497 bytes in size.

FIELD OF THE INVENTION

The present invention relates to the fields of molecular biology and nucleic acid chemistry. The invention provides methods and reagents for detecting pathogens, such as *Neisseria gonorrhoeae* and accordingly, also relates to the fields of medical diagnostics and prognostics. In particular, the invention relates to polynucleotides and methods for amplifying and detecting *Neisseria gonorrhoeae*.

BACKGROUND OF THE INVENTION

*Neisseria gonorrhoeae*, the etiological agent of gonorrhea, infects the urogenital tract with clinical signs of gonorrhea often overlapping with those of other sexually transmitted diseases (STDs). Infection, often asymptomatic in women, if left untreated can lead to more serious and permanent health related complications such as pelvic inflammatory disease (PID), chronic pelvic pain, tubal infertility, and life-threatening ectopic pregnancy. In men, the majority of urethral infections cause urethritis, occasionally resulting in epididymitis which can lead to infertility if not treated. Though not as common, asymptomatic infection rates among men are also significant. Among neonates, conjunctivitis can result in blindness. Among all three groups, untreated *N. gonorrhoeae* can disseminate leading to acute dermatitis, tenosynovitis syndrome and sepsis associated with arthritis, meningitis, or endocarditis.

*N. gonorrhoeae* has a global impact estimate of 106 million new cases annually. Worldwide, *N. gonorrhoeae* is the second most prevalent bacterial STD as well as the second most common notifiable communicable disease in the United States. The WHO estimates incidence of *N. gonorrhoeae* infection has been steadily rising since 1995, with an increase of 11.7% from 2005 to 2008. Compounding the clinical and increased incidence concerns is the categorization of *N. gonorrhoeae* as an immediate public health threat related to its antibiotic resistance profile, with 30% of strains estimated to carry resistance to one or more treatment antibiotics.

One of the main public health strategies in prevention and reduction of infectious disease is reducing person-to-person spread through screening, prompt identification and effective treatment. Imperative to this strategy are specific and sensitive diagnostics.

The performance of nucleic acid amplification tests (NAATs) as measured by sensitivity, specificity, and ease of specimen transport exceeds that of any other testing diagnostic currently available for diagnosing gonococcal infections. The US Centers for Disease Control (CDC) specifically recommends use of NAATs by clinical and disease control laboratories to detect gonorrhea with a few limited exceptions. Recommendations for the Laboratory-Based Detection of *Chlamydia trachomatis* and *Neisseria gonorrhoeae*—2014. MMWR 2014; 63 (No. RR-2). Related to the sensitivity and specificity, these assays have provided for the use of less invasive specimen collection, which better facilitates infectious disease screening. Optimal recommended specimen types for NAATs include first catch urine from men and vaginal swabs from women.

FDA-cleared NAATs included Abbott RealTime CT/NG (Abbott m2000 system platform), Aptima COMBO or individual CT or GC assays (Hologic Panther system platform), BD ProbeTec assays (ET CT/GC Amplified DNA assay and $Q^x$ CT or GC Amplified DNA assays and BD Viper system platform), Cepheid Xpert CT/NG assay (GeneXpert IV point of care device), and Roche Diagnostics CT/NG tests (cobas 4800 system platform). The Abbott, Aptima, BD, and Roche assays all include automation for sample preparation, target amplification, and detection. While this is a benefit from a sample preparation and limited hands on time perspective, each system platform translates into a large investment in capital equipment and requires at least 3 hours to reach a diagnostic result. The Cepheid assay and its accompanying device is the only point of care instrument, with reduced cost, spatial fingerprint, but still requires approximately 90 minutes to generate a diagnostic result.

What is needed, therefore, are new assays compatible with point of care devices that offer high sensitivity, significantly reduced time to answer, reduced equipment cost, and the potential for sample in answer out utilization.

SUMMARY

In some embodiments, provided herein is a composition comprising a set of polynucleotides selected from the group consisting of Set-1 through Set-27. In some embodiments, the composition further comprises a probe. In some embodiments, the probe comprises a label. In some embodiments, the probe is a labeled polynucleotide.

In some embodiments, the probe is a labeled polynucleotide having a sequence selected from the group consisting of SEQ ID NO: 73-76 and the set of polynucleotides is selected from Sets 12-15.

In some embodiments, the label is a fluorophore. In some embodiments, the fluorophore is covalently attached to a terminus of the polynucleotide. In some embodiments, the probe is a molecular beacon comprising a quencher. In some embodiments, the fluorophore is FAM and the quencher is BHQ1. In other embodiments, the fluorophore is ATTO 565 or Alexa 594 and the quencher is BHQ1 or BHQ2.

Also provided herein is a molecular beacon comprising a fluorophore, a quencher and a polynucleotide, wherein the polynucleotide is selected from the group consisting of SEQ ID NOs: 73-76 and the set of polynucleotides is selected from Sets 12-15. In some embodiments, the fluorophore is FAM and the quencher is BHQ1. In other embodiments, the fluorophore is ATTO 565 or Alexa 594 and the quencher is BHQ1 or BHQ2.

Also provided herein is a method of detecting *Neisseria gonorrhoeae* in a test sample, the method comprising: (a) extracting nucleic acid from the test sample; (b) amplifying a target sequence by reacting the nucleic acid extracted in step (a) with a reaction mixture comprising a strand displacement DNA polymerase and a sequence-specific primer set, wherein said sequence-specific primer set is selected from the group consisting of Set-1 through Set-27; and (c) detecting the presence or absence of an amplified product of step (b); wherein the presence of said amplification product is indicative of the presence of Neisseria gonorrhoeae in the test sample.

In some embodiments of the method of detecting Neisseria gonorrhoeae in a test sample, the amplification in step (b) of the target sequence is performed at between about 60° C. and 67° C. for less than 30 minutes. In some embodiments, the amplification step is performed for less than 15 minutes. In some embodiments, the amplification step is performed for less than ten minutes.

In some embodiments of the method of detecting Neisseria gonorrhoeae in a test sample, detecting the presence or absence of the amplification product comprises hybridizing the amplified product with a probe comprising a polynucleotide attached to a label.

In some embodiments of the method of detecting Neisseria gonorrhoeae in a test sample, the polynucleotide comprises a sequence selected from the group consisting of SEQ ID NO: 73-76 and the sequence-specific primer set is selected from Sets 12-15.

In some embodiments of the method of detecting Neisseria gonorrhoeae in a test sample, the probe is a molecular beacon. In some embodiments, the reaction mixture further comprises a reverse transcriptase. In some embodiments, Neisseria gonorrhoeae is present in the test sample at a concentration of ≤100 CFU/mL. In some embodiments, Neisseria gonorrhoeae is present in the test sample at a concentration of ≤10 CFU/mL.

Also provided herein, according to some embodiments of the invention, is a kit comprising a composition comprising a set of polynucleotides selected from the group consisting of Set-1 through Set-27 and amplification reagents. In some embodiments, the amplification reagents comprise a strand displacement polymerase. In some embodiments, the kit further comprises a probe.

Also provided herein is a method of detecting Neisseria gonorrhoeae in a test sample, the method comprising: (a) extracting nucleic acid from the test sample; (b) amplifying a target sequence by reacting the nucleic acid extracted in step (a) for less than twenty minutes with a reaction mixture comprising a strand displacement DNA polymerase and a sequence-specific LAMP primer set; and (c) detecting the presence or absence of an amplified product of step (b); wherein the presence of said amplification product is indicative of the presence of Neisseria gonorrhoeae in the test sample.

In some embodiments of the method, the nucleic acid is reacted with the reaction mixture for less than fifteen minutes. In some embodiments of the method, the target sequence is located in the cytochrome C peroxidase (ccpA) gene of Neisseria gonorrhoeae.

In some embodiments of the method, Neisseria gonorrhoeae is present in the test sample at a concentration of ≤100 CFU/mL. In some embodiments of the method, Neisseria gonorrhoeae is present in the test sample at a concentration of ≤10 CFU/mL.

In some embodiments of the method, the test sample comprises one or more other microorganisms in addition to Neisseria gonorrhoeae, and wherein the target sequence from Neisseria gonorrhoeae is preferentially amplified over a polynucleotide sequence from the one or more other microorganisms.

In some embodiments, the invention provides a nucleic acid sequence at least 90%, at least 95%, at least 96%, at least 97%, at least 98%, at least 99%%, at least 99.1%, at least 99.2%, at least 99.3%, at least 99.4%, at least 99.5%, at least 99.6%, at least 99.7%, at least 99.8% or at least 99.9% identical to SEQ ID NOs 1-76 and methods of using those nucleic acid sequences to detect Neisseria gonorrhoeae in a test sample.

DETAILED DESCRIPTION

Detecting low concentrations of species (down to a few molecules or microorganisms in a sample) is a challenge in medicine. The present invention relates to the selective detection of Neisseria gonorrhoeae. In particular, based on new detection strategies utilizing nucleic acid amplification, particularly RT-LAMP, and molecular beacon detection, N. gonorrhoeae infections can be diagnosed using the methods and reagents described herein. Using RNA (either ribosomal RNA (rRNA) or messenger RNA) as the target regions provides multiple copies of the target per N. gonorrhoeae genome. Accordingly, this facilitates the detection of N. gonorrhoeae in samples utilizing the approaches described herein relative to techniques that target genomic DNA, even when present in multiple copies per genome. In addition, the molecular beacon detection reagents described herein provide additional specificity, failing to bind, in most cases, to off target amplified DNA, thereby minimizing the occurrence of, e.g., false positives. This specificity is illustrated in, inter alia, Example 3 (Tables 4 and 5) provided below. Many other features of the invention are also described herein.

As used herein, "nucleic acid" includes both DNA and RNA, including DNA and RNA containing non-standard nucleotides. A "nucleic acid" contains at least one polynucleotide (a "nucleic acid strand"). A "nucleic acid" may be single-stranded or double-stranded. The term "nucleic acid" refers to nucleotides and nucleosides which make up, for example, deoxyribonucleic acid (DNA) macromolecules and ribonucleic acid (RNA) macromolecules. The most common nucleic acids are deoxyribonucleic acid (DNA) and ribonucleic acid (RNA). It should be further understood that the present invention can be used for biological sequences containing artificial nucleotides such as peptide nucleic acid (PNA), morpholino, locked nucleic acid (LNA), glycol nucleic acid (GNA) and threose nucleic acid (TNA), among others. Preferably, the artificial nucleotides are locked nucleic acid molecules, including [alpha]-L-LNAs. LNAs comprise ribonucleic acid analogues wherein the ribose ring is "locked" by a methylene bridge between the 2'-oxygen and the 4'-carbon—i.e., oligonucleotides, containing at least one LNA monomer, that is, one 2'-O,4'-C-methylene-β-D-ribofuranosyl nucleotide. LNA bases form standard Watson-Crick base pairs but the locked configuration increases the rate and stability of the base-pairing reaction (Jepsen et al., Oligonucleotides, 14, 130-146 (2004)).

As used herein, a "polynucleotide" refers to a polymeric chain containing two or more nucleotides, which contain deoxyribonucleotides, ribonucleotides, and/or their analog, such as those containing modified backbones (e.g. peptide nucleic acids (PNAs) or phosphorothioates) or modified bases. "Polynucleotides" includes primers, oligonucleotides, nucleic acid strands, etc. A polynucleotide may contain standard or non-standard nucleotides. Thus, the term includes mRNA, tRNA, rRNA, ribozymes, DNA, cDNA, recombinant nucleic acids, branched nucleic acids, plasmids, vectors, probes, primers, etc. Typically, a polynucleotide contains a 5' phosphate at one terminus ("5' terminus") and a 3' hydroxyl group at the other terminus ("3' terminus") of the chain. The most 5' nucleotide of a polynucleotide may be referred to herein as the "5' terminal nucleotide" of the polynucleotide. The most 3' nucleotide of a polynucleotide may be referred to herein as the "3' terminal nucleotide" of the polynucleotide. Where nucleic acid of the invention takes the form of RNA, it may or may not have a 5' cap.

LAMP is a nucleic acid amplification method that relies on auto-cycle strand-displacement DNA synthesis performed by a Bst DNA polymerase or another strand displacement polymerase. The amplified products are stem-loop structures with several repeated sequences of the target and multiple loops. The principal merit of this method is that denaturation of the DNA template is not required, and thus the LAMP reaction can be conducted under isothermal conditions (ranging from 60 to 67° C.). LAMP requires only one enzyme and four types of primers that recognize six distinct hybridization sites in the target sequence. The reaction can be accelerated by the addition of two additional primers. The method produces a large amount of amplified product, resulting in easier detection, such as detection by visual judgment of the turbidity or fluorescence of the reaction mixture.

In brief, the reaction is initiated by annealing and extension of a pair of 'loop-forming' primers (forward and backward inner primers, FIP and BIP, respectively), followed by annealing and extension of a pair of flanking primers (F3 and B3). Extension of these primers results in strand-displacement of the loop-forming elements, which fold up to form terminal hairpin-loop structures. Once these key structures have appeared, the amplification process becomes self-sustaining, and proceeds at constant temperature in a continuous and exponential manner (rather than a cyclic manner, like PCR) until all of the nucleotides (dATP, dTTP, dCTP & dGTP) in the reaction mixture have been incorporated into the amplified DNA, or the chemical reaction is otherwise exhausted. Optionally, an additional pair of primers can be included to accelerate the reaction. These primers, termed "loop primers," hybridize to non-inner primer bound terminal loops of the inner primer dumbbell-shaped products.

The term "primer" as used herein refers to an oligonucleotide, which is capable of acting as a point of initiation of synthesis when placed under conditions in which synthesis of primer extension product which is complementary to a nucleic acid strand (template) is induced, i.e., in the presence of nucleotides and an agent for polymerization, such as DNA polymerase, and at a suitable temperature and pH.

LAMP allows amplification of target DNA sequences with higher sensitivity and specificity than PCR, often with reaction times below 30 minutes, which is equivalent to the fastest real-time PCR tests. The target sequence which is amplified is typically 200-300 base-pairs (bp) in length, and the reaction relies upon recognition of between 120 bp and 180 bp of this sequence by several primers simultaneously during the amplification process. This high level of stringency makes the amplification highly specific, such that the appearance of amplified DNA in a reaction occurs only if the entire target sequence was initially present.

Applications for LAMP have been further extended to include detection of RNA molecules by addition of Reverse Transcriptase enzyme (RT). By including RNA detection, the types of targets for which LAMP can be applied are also expanded and add the ability to additionally target RNA-based viruses, important regulatory non-coding RNA (sRNA, miRNA), and RNA molecules that have been associated with particular disease or physiological states. The ability to detect RNA also has the potential to increase assay sensitivity, for instance in choosing highly expressed, stable, and/or abundant messenger RNA (mRNA) or ribosomal RNA (rRNA) targets. This preliminary phase of amplification involves the reverse transcription of RNA molecules to complementary DNA (cDNA). The cDNA then serves as template for the strand displacing DNA polymerase. Use of a thermostable RT enzyme (i.e., NEB RTx) enables the reaction to be completed at a single temperature and in a one step, single mix reaction.

A "target sequence," as used herein, means a nucleic acid sequence of *Neisseria gonorrhoeae*, or complement thereof, that is amplified, detected, or both amplified and detected using one or more of the polynucleotides herein provided. Additionally, while the term target sequence sometimes refers to a double stranded nucleic acid sequence, those skilled in the art will recognize that the target sequence also can be single stranded, e.g., RNA. A target sequence may be selected that is more or less specific for a particular organism. For example, the target sequence may be specific to an entire genus, to more than one genus, to a species or subspecies, serogroup, auxotype, serotype, strain, isolate or other subset of organisms.

The speed, specificity and sensitivity of the primers/probe compositions and method described herein result from several aspects. Exemplary primers for use in the compositions and methods according to the present invention include:

TABLE 1

LAMP primers

| Seq ID | Sequence (5' to 3') |
|---|---|
| SEQ ID NO: 1 | CATAAGGAATACACGATGTCTTTC |
| SEQ ID NO: 2 | GATTTTCTGCATTTCTTCGACA |
| SEQ ID NO: 3 | AAGCAGGAGAAGCATCGCCTATTGGCATTGTCTTCACTGT |
| SEQ ID NO: 4 | CGCCCGAAGACCAAGACCGTCGGCAAAGGTTGGAATA |
| SEQ ID NO: 5 | GCCGCAGACTTTTCCTGA |
| SEQ ID NO: 6 | TTTGAAACGCGCGCAAG |
| SEQ ID NO: 7 | AAGGCAACGTCAACGC |
| SEQ ID NO: 8 | GTCAGCACGGCCTTTG |
| SEQ ID NO: 9 | CACCGTTGTGGCAGGCACTGAGCGAACAGGAACG |
| SEQ ID NO: 10 | CAACCTTGGAGGCACGACCTGAATTTCCAATACGGCCC |
| SEQ ID NO: 11 | GTTGTCCATGAACGCGC |
| SEQ ID NO: 12 | CAGAAATTCGGTCTGGTCCA |
| SEQ ID NO: 13 | TATTCCAACCTTTGCCGAC |
| SEQ ID NO: 14 | GCCGAACTGCCCTTTG |
| SEQ ID NO: 15 | CTTTGGAAAGGCGTGGTTCATACCCGTTTACCGAAGAACAGG |
| SEQ ID NO: 16 | CAAAGGCAATACCGTAAGCTGCCATATTGTCCACACCGGC |

TABLE 1-continued

LAMP primers

| Seq ID | Sequence (5' to 3') |
|---|---|
| SEQ ID NO: 17 | CAGAGTTGGTGTCCGAGTT |
| SEQ ID NO: 18 | CTTGCCACAACCTTGCTTC |
| SEQ ID NO: 19 | TATTTCCACAACGGCAGC |
| SEQ ID NO: 20 | GGCTTAGATTCCATCGGTG |
| SEQ ID NO: 21 | CCACATCTTCTTTCGGAATGTCTTTTGGGAGCTGGATAAGGC |
| SEQ ID NO: 22 | GTGGATAACATCGTCGTATTCCTGACAGTTCCGGCATCGTG |
| SEQ ID NO: 23 | CAATTGCGCCTTACCCATG |
| SEQ ID NO: 24 | CTTTCCGGCAATGTTTCCG |
| SEQ ID NO: 25 | TTGTCGCGTTTCGGATC |
| SEQ ID NO: 26 | CCAACCTTTGCCGACTG |
| SEQ ID NO: 27 | CATCACTACCGCATTGGG |
| SEQ ID NO: 28 | CAGACCGAATTTCTGGAAGG |
| SEQ ID NO: 29 | GCTCAGGGCGTTGACGTGTTTGAGCGTACCTGC |
| SEQ ID NO: 30 | GCGCGTTCATGGACAACGCGTGCCTCCAAGGTTG |
| SEQ ID NO: 31 | CCATTTGGTCGGCGTCA |
| SEQ ID NO: 32 | GCTGTATTGCCTGCCACA |
| SEQ ID NO: 33 | CTTAGATTCCATCGGTGCG |
| SEQ ID NO: 34 | GGCAATGTTTCCGAATCAGC |
| SEQ ID NO: 35 | GCGATGCTTCTCCTGC |
| SEQ ID NO: 36 | GTGTCCGAGTTTGACCTG |
| SEQ ID NO: 37 | GAAGCGGAAGGAACGGCTTTTCCGAGACCGAAGCG |
| SEQ ID NO: 38 | CTCGCCCGAAGACCAAGACTCTGCATTTCTTCGACAGTC |
| SEQ ID NO: 39 | GGCCTGTACTTGGGAAGC |
| SEQ ID NO: 40 | GCGCAAGGTGTATTCCAAC |
| SEQ ID NO: 41 | GTGTCCGAGTTTGACCTGT |
| SEQ ID NO: 42 | CAACCTTGCTTCCGCC |
| SEQ ID NO: 43 | TCATTCGCCATTTCCACC |
| SEQ ID NO: 44 | ATGCGGTAGGCGAGTTGCGTGGACAATATGCCGACC |
| SEQ ID NO: 45 | GGGCAGCCAGTTTTGGGAGATTCACCAAAGGCCCG |
| SEQ ID NO: 46 | CCCTTTGTGCCCCTGAC |
| SEQ ID NO: 47 | GTGCCGCCGATGTTGA |
| SEQ ID NO: 48 | AACTCGGACACCAACTC |
| SEQ ID NO: 49 | CATTCAATGCGGTAGGC |

TABLE 1-continued

LAMP primers

| Seq ID | Sequence (5' to 3') |
|---|---|
| SEQ ID NO: 50 | AGCAAGGTTGTGGCAAGAGGGTATGAACCACGCCTT |
| SEQ ID NO: 51 | CGCCGGTGTGGACAATGAACTGCCCTTTGTGC |
| SEQ ID NO: 52 | CAGCTTACGGTATTGCCTT |
| SEQ ID NO: 53 | ATGCCGACCAGTCAGG |
| SEQ ID NO: 54 | ATATGCCGACCAGTCAG |
| SEQ ID NO: 55 | GGGAACTTTGGCGATTT |
| SEQ ID NO: 56 | AGCAGCGCAGCATTCAATGCACAAAGGGCAGTTC |
| SEQ ID NO: 57 | TGTTGAAGAACAGGCTGGCGCGAATCATTCGCCATT |
| SEQ ID NO: 58 | GTAGGCGAGTTGCGTC |
| SEQ ID NO: 59 | TTGGTGAATCCGGTGGA |
| SEQ ID NO: 60 | GAGTTGCGTCCGCCGAACTGCCTCTTGCCACAACCTTGCTTCCG |
| SEQ ID NO: 61 | ACCGCATTGAATGCTGCGCTGCTGCCCGCCAGCCTGTTCTTC |
| SEQ ID NO: 62 | TGACTGGTCGGCATATTGTCCACAC |
| SEQ ID NO: 63 | CGGACGTGCCGCCGATGTT |
| SEQ ID NO: 64 | CCTTTCCAAAGGCAATACCGTAAGC |
| SEQ ID NO: 65 | TCGCCATTTCCACCGGATTCAC |
| SEQ ID NO: 66 | TGCGGTAGGCGAGTTGCGGGACAATATGCCGACCAGT |
| SEQ ID NO: 67 | TTGAATGCTGCGCTGCTGGCAGCCTGTTCTTCAACATCG |
| SEQ ID NO: 68 | CGAACTGCCCTTTGTGCC |
| SEQ ID NO: 69 | TTGGGACGGACGTGCC |
| SEQ ID NO: 70 | TGCCACAACCTTGCTTCC |
| SEQ ID NO: 71 | CGAATCATTCGCCATTTCCA |
| SEQ ID NO: 72 | CTTTGGAAAGGCGTGGTTCATACAAATCCGTCCGTTTACCG |

Detection of the LAMP amplified products can be achieved via a variety of methods. In a preferred embodiment, detection of product is conducted by adding a fluorescently-labeled probe to the primer mix. The term used herein "probe" refers to a single-stranded nucleic acid molecule comprising a portion or portions that are complementary, or substantially complementary, to a target sequence. In certain implementations, the fluorescently-labeled probe is a molecular beacon.

As used herein, "molecular beacon" refers to a single stranded hairpin-shaped oligonucleotide probe designed to report the presence of specific nucleic acids in a solution. A molecular beacon consists of four components; a stem, hairpin loop, end-labelled fluorophore and opposite end-labelled quencher (Tyagi et al., (1998) Nature Biotechnology 16:49-53). When the hairpin-like beacon is not bound to a target, the fluorophore and quencher lie close together and fluorescence is suppressed. In the presence of a complementary target nucleotide sequence, the stem of the beacon opens to hybridize to the target. This separates the fluorophore and quencher, allowing the fluorophore to fluoresce. Alternatively, molecular beacons also include fluorophores that emit in the proximity of an end-labelled donor. "Wavelength-shifting Molecular Beacons" incorporate an additional harvester fluorophore enabling the fluorophore to emit more strongly. Current reviews of molecular beacons include Wang et al., 2009, *Angew Chem Int Ed Engl*, 48(5):856-870; Cissell et al., 2009, *Anal Bioanal Chem* 393(1):125-35; Li et al., 2008, *Biochem Biophys Res Comm* 373(4):457-61; and Cady, 2009, *Methods Mol Biol* 554:367-79.

In one implementation, the molecular beacon comprises a fluorophore, a quencher, and a polynucleotide, wherein the polynucleotide comprises a sequence selected from the group consisting of SEQ ID NOS: 73-76. In some embodiments, the polynucleotide comprises a sequence selected from the group consisting of nucleotides 6-22 of SEQ ID NO: 73, nucleotides 5-24—of SEQ ID NO: 74, nucleotides 3-21 of SEQ ID NO: 75, and nucleotides 3-24 of SEQ ID NO: 76. The polynucleotides having the sequences described above can include one or more non-natural nucleosides or linkages, such as peptide nucleic acid (PNA), morpholino, locked nucleic acid (LNA), glycol nucleic acid (GNA) and threose nucleic acid (TNA), among others. In some embodiments, the polynucleotide of the molecular beacon comprises one to six locked nucleic acids. In a preferred embodiment, the polynucleotide of the molecular beacon comprises three locked nucleic acids. In another preferred embodiment, the polynucleotide of the molecular beacon comprises four locked nucleic acids.

The term "label" as used herein means a molecule or moiety having a property or characteristic which is capable of detection and, optionally, of quantitation. A label can be directly detectable, as with, for example (and without limitation), radioisotopes, fluorophores, chemiluminophores, enzymes, colloidal particles, fluorescent microparticles and the like; or a label may be indirectly detectable, as with, for example, specific binding members. It will be understood that directly detectable labels may require additional components such as, for example, substrates, triggering reagents, quenching moieties, light, and the like to enable detection and/or quantitation of the label. When indirectly detectable labels are used, they are typically used in combination with a "conjugate". A conjugate is typically a specific binding member that has been attached or coupled to a directly detectable label. Coupling chemistries for synthesizing a conjugate are well known in the art and can include, for example, any chemical means and/or physical means that does not destroy the specific binding property of the specific binding member or the detectable property of the label. As used herein, "specific binding member" means a member of a binding pair, i.e., two different molecules where one of the molecules through, for example, chemical or physical means specifically binds to the other molecule. In addition to antigen and antibody specific binding pairs, other specific binding pairs include, but are not intended to be limited to, avidin and biotin; haptens and antibodies specific for haptens; complementary nucleotide sequences; enzyme cofactors or substrates and enzymes; and the like.

The molecular beacon can be composed of nucleic acid only such as DNA or RNA, or it can be composed of a peptide nucleic acid (PNA) conjugate. The fluorophore can be any fluorescent organic dye or a single quantum dot. The quenching moiety desirably quenches the luminescence of the fluorophore. Any suitable quenching moiety that quenches the luminescence of the fluorophore can be used. A fluorophore can be any fluorescent marker/dye known in the art. Examples of suitable fluorescent markers include, but are not limited to, Fam, Hex, Tet, Joe, Rox, Tamra, Max, Edans, Cy dyes such as Cy5, Fluorescein, Coumarin, Eosine, Rhodamine, Bodipy, Alexa, Cascade Blue, Yakima Yellow, Lucifer Yellow, Texas Red, and the family of ATTO dyes. A quencher can be any quencher known in the art. Examples of quenchers include, but are not limited to, Dabcyl, Dark Quencher, Eclipse Dark Quencher, ElleQuencher, Tamra, BHQ and QSY (all of them are Trade-Marks). The skilled person would know which combinations of dye/quencher are suitable when designing a probe. In an exemplary embodiment, fluorescein (FAM) is used in conjunction with Blackhole Quencher™ (BHQ™) (Novato, Calif.). Binding of the molecular beacon to amplified product can then be directly, visually assessed. Alternatively, the fluorescence level can be measured by spectroscopy in order to improve sensitivity.

A variety of commercial suppliers produce standard and custom molecular beacons, including Abingdon Health (UK; www.abingdonhealth.com), Attostar (US, MN; www.attostar.com), Biolegio (NLD; www.biolegio.com), Biomers.net (DEU; www.biomers.net), Biosearch Technologies (US, CA; www.biosearchtech.com), Eurogentec (BEL; www.eurogentec.com), Gene Link (US, NY; www.genelink.com) Integrated DNA Technologies (US, IA; www.idtdna.com), Isogen Life Science (NLD; www.isogen-lifescience.com), Midland Certified Reagent (US, TX; www.oligos.com), Eurofins (DEU; www.eurofinsgenomics.eu), Sigma-Aldrich (US, TX; www.sigmaaldrich.com), Thermo Scientific (US, MA; www.thermoscientific.com), TIB MOLBIOL (DEU; www.tib-molbiol.de), TriLink Bio Technologies (US, CA; www.trilinkbiotech.com). A variety of kits, which utilize molecular beacons are also commercially available, such as the Sentinel™ Molecular Beacon Allelic Discrimination Kits from Stratagene (La Jolla, Calif.) and various kits from Eurogentec SA (Belgium, eurogentec.com) and Isogen Bioscience BV (The Netherlands, isogen.com).

The oligonucleotide probes and primers of the invention are optionally prepared using essentially any technique known in the art. In certain embodiments, for example, the oligonucleotide probes and primers described herein are synthesized chemically using essentially any nucleic acid synthesis method, including, e.g., according to the solid phase phosphoramidite triester method described by Beaucage and Caruthers (1981), Tetrahedron Setts. 22(20): 1859-1862, which is incorporated by reference, or another synthesis technique known in the art, e.g., using an automated synthesizer, as described in Needham-VanDevanter et al. (1984) Nucleic Acids Res. 12:6159-6168, which is incorporated by reference. A wide variety of equipment is commercially available for automated oligonucleotide synthesis. Multi-nucleotide synthesis approaches (e.g., tri-nucleotide synthesis, etc.) are also optionally utilized. Moreover, the primer nucleic acids described herein optionally include various modifications. To further illustrate, primers are also optionally modified to improve the specificity of amplification reactions as described in, e.g., U.S. Pat. No. 6,001,611, issued Dec. 14, 1999, which is incorporated by reference. Primers and probes can also be synthesized with various other modifications as described herein or as otherwise known in the art.

In addition, essentially any nucleic acid (and virtually any labeled nucleic acid, whether standard or non-standard) can be custom or standard ordered from any of a variety of commercial sources, such as Integrated DNA Technologies, the Midland Certified Reagent Company, Eurofins, Biosearch Technologies, Sigma Aldrich and many others.

Test samples are generally derived or isolated from subjects, typically mammalian subjects, more typically human subjects, suspected of having a *N. gonorrhoeae* infection. Exemplary samples or specimens include blood, plasma, serum, urine, synovial fluid, seminal fluid, seminal plasma, prostatic fluid, vaginal fluid, cervical fluid, uterine fluid, cervical scrapings, amniotic fluid, anal scrapings, mucus, sputum, tissue, and the like. Essentially any technique for acquiring these samples is optionally utilized including, e.g., scraping, venipuncture, swabbing, biopsy, or other techniques known in the art.

The term "test sample" as used herein, means a sample taken from an organism or biological fluid that is suspected of containing or potentially contains a target sequence. The test sample can be taken from any biological source, such as for example, tissue, blood, saliva, sputa, mucus, sweat, urine, urethral swabs, cervical swabs, vaginal swabs, urogenital or anal swabs, conjunctival swabs, ocular lens fluid, cerebral spinal fluid, milk, ascites fluid, synovial fluid, peritoneal fluid, amniotic fluid, fermentation broths, cell cultures, chemical reaction mixtures and the like. The test sample can be used (i) directly as obtained from the source or (ii) following a pre-treatment to modify the character of the sample. Thus, the test sample can be pre-treated prior to use by, for example, preparing plasma or serum from blood, disrupting cells or viral particles, preparing liquids from solid materials, diluting viscous fluids, filtering liquids, distilling liquids, concentrating liquids, inactivating interfering components, adding reagents, purifying nucleic acids, and the like.

Advantageously, the invention enables reliable rapid detection of *Neisseria gonorrhoeae* in a clinical sample, such as a urine sample.

To further illustrate, prior to analyzing the target nucleic acids described herein, those nucleic acids may be purified or isolated from samples that typically include complex mixtures of different components. Cells in collected samples are typically lysed to release the cell contents. For example, *N. gonorrhoeae* and other cells in the particular sample can be lysed by contacting them with various enzymes, chemicals, and/or lysed by other approaches known in the art, which degrade, e.g., bacterial cell walls. In some embodiments, nucleic acids are analyzed directly in the cell lysate. In other embodiments, nucleic acids are further purified or extracted from cell lysates prior to detection. Essentially any nucleic acid extraction methods can be used to purify nucleic acids in the samples utilized in the methods of the present invention. Exemplary techniques that can be used to purifying nucleic acids include, e.g., affinity chromatography, hybridization to probes immobilized on solid supports, liquid-liquid extraction (e.g., phenol-chloroform extraction, etc.), precipitation (e.g., using ethanol, etc.), extraction with filter paper, extraction with micelle-forming reagents (e.g., cetyl-trimethyl-ammonium-bromide, etc.), binding to immobilized intercalating dyes (e.g., ethidium bromide, acridine, etc.), adsorption to silica gel or diatomic earths, adsorption to magnetic glass particles or organo-silane particles under chaotropic conditions, and/or the like. Sample processing is also described in, e.g., U.S. Pat. Nos. 5,155,018, 6,383,393, and 5,234,809, which are each incorporated by reference.

A test sample may optionally have been treated and/or purified according to any technique known by the skilled person, to improve the amplification efficiency and/or qualitative accuracy and/or quantitative accuracy. The sample may thus exclusively, or essentially, consist of nucleic acid(s), whether obtained by purification, isolation, or by chemical synthesis. Means are available to the skilled person, who would like to isolate or purify nucleic acids, such as DNA, from a test sample, for example to isolate or purify DNA from cervical scrapes (e.g., QIAamp-DNA Mini-Kit; Qiagen, Hilden, Germany).

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1: Target Selection, Sequence Analysis and Assay Design

Sequences for *Neisseria gonorrhoeae* and closely related species including *Neisseria meningitidis*, *Neisseria lactamica*, *Neisseria sicca* and *Neisseria cinerea* were obtained from the National Center for Biotechnology Information (NCBI) or Pathosystems Resource Integration Center (PATRIC) databases. Sequences were aligned using Clustal Omega (Sievers, et al. (2011). Molecular Systems Biology 7:539) or MAFFT (Katoh, Standley 2013. *Molecular Biology and Evolution* 30:772-780) and regions unique to *N. gonorrhoeae* were selected for primer and molecular beacon probe design.

Primer/probe-based detection assays were designed to utilize isothermal loop mediated amplification targeting RNA through the addition of a Reverse transcriptase (RT-LAMP) to the reaction. A molecular beacon probe with 5' fluorophore/3' quencher modifications, 6-Carboxyfluorescein and Black Hole Quencher 1, was included to provide target-specific fluorescent detection. *N. gonorrhoeae* RT-LAMP primer sets (Table 1 and Table 2) were designed using a combination of software programs including PremierBiosoft's LAMP Designer, Beacon Designer, an in-house script and manual designs. Resultant predicted amplicons were additionally Blasted against the NCBI nucleotide database, including the human transcriptome, and against individual non-*gonorrhoeae* species within the genus *Neisseria* to further predict assay specificity.

The inventive primer sets are summarized in Table 2, which include, at a minimum, a forward inner primer (FIP) and backward inner primer (BIP). Additionally, the primer sets typically also include at least two additional primers selected from the forward outer primer (F3), backward outer primer (B3), forward loop primer (LF) and backward loop primer (LB).

TABLE 2

LAMP Primer Sets

| Set | F3 | B3 | FIP | BIP | LF | LB |
|---|---|---|---|---|---|---|
| Set-1  | SEQ ID NO: 1  | SEQ ID NO: 2  | SEQ ID NO: 3  | SEQ ID NO: 4  | SEQ ID NO: 5  | SEQ ID NO: 6 |
| Set-2  | SEQ ID NO: 7  | SEQ ID NO: 8  | SEQ ID NO: 9  | SEQ ID NO: 10 | SEQ ID NO: 11 | SEQ ID NO: 12 |
| Set-3  | SEQ ID NO: 13 | SEQ ID NO: 14 | SEQ ID NO: 15 | SEQ ID NO: 16 | SEQ ID NO: 17 | SEQ ID NO: 18 |
| Set-4  | SEQ ID NO: 19 | SEQ ID NO: 20 | SEQ ID NO: 21 | SEQ ID NO: 22 | SEQ ID NO: 23 | SEQ ID NO: 24 |
| Set-5  | SEQ ID NO: 13 | SEQ ID NO: 25 | SEQ ID NO: 9  | SEQ ID NO: 10 | SEQ ID NO: 11 | SEQ ID NO: 12 |
| Set-6  | SEQ ID NO: 26 | SEQ ID NO: 14 | SEQ ID NO: 15 | SEQ ID NO: 16 | SEQ ID NO: 17 | SEQ ID NO: 18 |
| Set-7  | SEQ ID NO: 27 | SEQ ID NO: 28 | SEQ ID NO: 29 | SEQ ID NO: 30 | SEQ ID NO: 31 | SEQ ID NO: 32 |
| Set-8  | SEQ ID NO: 19 | SEQ ID NO: 33 | SEQ ID NO: 21 | SEQ ID NO: 22 | SEQ ID NO: 23 | SEQ ID NO: 34 |
| Set-9  | SEQ ID NO: 35 | SEQ ID NO: 36 | SEQ ID NO: 37 | SEQ ID NO: 38 | SEQ ID NO: 39 | SEQ ID NO: 40 |
| Set-10 | SEQ ID NO: 13 | SEQ ID NO: 14 | SEQ ID NO: 72 | SEQ ID NO: 16 | SEQ ID NO: 41 | SEQ ID NO: 18 |
| Set-11 | SEQ ID NO: 42 | SEQ ID NO: 43 | SEQ ID NO: 44 | SEQ ID NO: 45 | SEQ ID NO: 46 | SEQ ID NO: 47 |
| Set-12 | SEQ ID NO: 48 | SEQ ID NO: 49 | SEQ ID NO: 50 | SEQ ID NO: Si | SEQ ID NO: 52 | SEQ ID NO: 53 |
| Set-13 | SEQ ID NO: 54 | SEQ ID NO: 55 | SEQ ID NO: 56 | SEQ ID NO: 57 | SEQ ID NO: 58 | SEQ ID NO: 59 |
| Set-14 | SEQ ID NO: 64 | SEQ ID NO: 65 | SEQ ID NO: 60 | SEQ ID NO: 61 | SEQ ID NO: 62 | SEQ ID NO: 63 |
| Set-15 | SEQ ID NO: 70 | SEQ ID NO: 71 | SEQ ID NO: 66 | SEQ ID NO: 67 | SEQ ID NO: 68 | SEQ ID NO: 69 |

Typically, 3 to 5 μL of extracted nucleic acid material or negative controls (NU negative urine; NTC=nuclease free water or Tris buffer, no template control) served as template for RT-LAMP reactions. 10-25 μl total volume reactions were prepared on ice as mixes containing formulations including 1× amplification buffer comprising 10-40 mM Tris-HCl, 0-0.5% Tween 20, 0-300 mM Trehalose, 5-70 mM KCl, 4-10 mM MgSO4, 10-20 mM (NH4)2SO4, 0-2 mM TCEP and 1.6-2 mM each dCTP, dGTP, dATP and dTTP. NEB Bst2 polymerase (NEB CN #M0537L) and RTx Warmstart reverse transcriptase (NEB CN #M0380S) enzymes. Primers (2 μM inner primers, 0.2 μM outer primers, and 0.8 μM Loop primers) were added to individual reactions or directly to master mixes as required per experimental design. Molecular beacons (0.2 μM) or 200 nM Yo-Pro-1, Yo-Pro-3 or To-Pro dye was also added to the master mix, as indicated in the examples below. Amplification reactions were prepared with the standard 6-primer mix or a 7-primer mix where indicated (Sets 16-27). Master mixes were distributed to individual sample templates, vortexed and centrifuged briefly and each reaction loaded into individual wells of a 96- or 384-well plate (Roche CN#4729692001 or BioRad CNhsI9605). Reactions were carried out at temperatures ranging from 60–67° C. and fluorescence monitored on either a Roche LightCycler 96 Real-Time PCR instrument or a BioRad CFX96 real time cycler. Target amplification was monitored via intercalating dye or molecular beacon probe binding to target resulting in release of molecular beacon fluorescence intramolecular quenching.

Example 2: LAMP with Dye Detection

A negative urine matrix was spiked with titred *N. gonorrhoeae* (serially diluted in PBS, Zeptometrix CN #0801482, ATCC CN#19424 or ATCC CN#49226). Nucleic acids were extracted from the spiked sample using standard extraction methods and the sample was amplified using LAMP primers (as described in Table 2). YoPro™ dye or a compatible wavelength version within the same dye set family (Life Technologies; green fluorescent carbocyanine nucleic acid stain) was used for the detection of the amplified product. The master mix was prepared as described in Example 1. Results are summarized in Table 3. NT indicates conditions not tested. "No Amp" indicates that no amplification was detected.

TABLE 3

Time to Positive (Dye Detection)

| Set | $5 \times 10^3$ CFU/mL | 5 CFU/mL | NTC | NU |
|---|---|---|---|---|
| Set-12 | 12.89 | 21.66 | No Amp | No Amp |
| Set-13 | 6.28 ± 0.18 | 9.22 ± 0.26 | 42.2 (1 of 2) | No Amp |
| Set-14 | 7.55 | 10.93 | 29.03 | 34.98 |
| Set-15 | 4.68 | 6.88 | 39.71 | 42.84 |
| Set-2 | 5.5 ± 0.099 | 7.94 ± 0.13 | 26.36 ± 1.46 | 45.18 ± 1.95 |
| Set-3 | 9.47 ± 0.11 | 13.64 ± 0.37 | No Amp | No Amp |
| Set-4 | 5.90 ± 0.03 | 8.63 ± 0.20 | 33.09 ± 5.23 | 34.87 ± 4.18 |
| Set-5 | 5.15 ± 0.15 | 7.57 ± 0.16 | 29.72 ± 10.81 | 24.31 ± 4.96 |
| Set-6 | 9.58 ± 0.01 | 14.10 ± 1.00 | No Amp | No Amp |
| Set-7 | 6.59 ± 0.01 | 9.42 ± 0.09 | No Amp | 35.84 ± 3.22 |
| Set-8 | 5.26 ± 0.19 | 7.57 ± 0.01 | 36.17 ± 1.19 | 29.5 ± 1.53 |
| Set-1 | 12.56 ± 0.94* (*5 × $10^2$ CFU/mL) | No Amp | No Amp | NT |
| Set-9 | 4.25 (*5 × $10^2$ CFU/mL) | 5.00 ± 0.68 | 37.31 (1 of 3) | NT |
| Set-10 | 7.42 (*5 × $10^2$ CFU/mL) | 11.18 ± 0.25 | No Amp | NT |
| Set-11 | 4.90 (*5 × $10^2$ CFU/mL) | 5.92 ± 1.15 | 25.522.15 (3 of 3) | NT |

Example 3: Specificity

A subset of the primer sets described in Example 2 were additionally tested for specificity by comparing reactions with 5×10³ and 5 CFU/mL of extracted *N. gonorrhoeae* nucleic acid template (NG) to reactions with 5×10⁵-1×10⁶ CFU/mL of extracted nucleic acid template from closely related *Neisseria* species (live titred stocks were purchased from Zeptometrix), *Neisseria meningitides* (NM), *Neisseria lactamica* (NL), and *Neisseria sicca* (NS), negative urine extractions, or no template controls (NTC). When the amplification reactions were performed as described in Example 1, a number of the primer sets tested demonstrated some level of cross-reactivity against additional *Neisseria* species (Table 4).

TABLE 4

| Set | $T_p$ NG 5 × 10³ CFU/mL | NL | NS | NM | NTC | Neg Urine |
|---|---|---|---|---|---|---|
| Set-12 | 12.89 | No Amp | No Amp | No Amp | No Amp | No Amp |
| Set-13 | 6.28 ± 0.18 | No Amp | No Amp | No Amp | 42.2 (1 of 2) | No Amp |
| Set-14 | 7.55 | 30.88 | 37.03 | No call | 29.03 | 34.98 |
| Set-15 | 4.68 | 35.38 | 49.98 | 47.75 | 39.71 | 42.84 |
| Set-2 | 5.5 ± 0.099 | 29.87 ± 13.72 | 44.95 ± 3.75 | 28.41 ± 11.02 | 26.36 ± 1.46 | 45.18 ± 1.95 |
| Set-3 | 9.47 ± 0.11 | No Amp | No Amp | No Amp | No Amp | No Amp |
| Set-4 | 5.90 ± 0.03 | 18.46 ± 4.28 | 18.53 ± 7.46 | 18.48 ± 7.55 | 33.09 ± 5.23 | 34.87 ± 4.18 |
| Set-5 | 5.15 ± 0.15 | 34.5 ± 0.55 | 22.10 ± 2.38 | 35.98 ± 9.96 | 29.72 ± 10.81 | 24.31 ± 4.96 |
| Set-6 | 9.58 ± 0.01 | No Amp | No Amp | No Amp | No Amp | No Amp |
| Set-7 | 6.59 ± 0.01 | 26.3 (1 of 2) | No Amp | No Amp | No Amp | 35.84 ± 3.22 |
| Set-8 | 5.26 ± 0.19 | 30.18 ± 3.00 | 30.45 ± 3.97 | 33.53 ± 5.54 | 36.17 ± 1.19 | 29.5 ± 1.53 |
| Set-1 | 12.56 ± 0.94* (*5 × 10² CFU/mL) | No Amp | No Amp | 24.33 ± 0.52 | No Amp | NT |
| Set-9 | 4.25 (*5 × 10² CFU/mL) | NT | NT | NT | 37.31 (1 of 3) | NT |
| Set-10 | 7.42 (*5 × 10² CFU/mL) | NT | NT | NT | No Amp | NT |
| Set-11 | 4.90 (*5 × 10² CFU/mL) | NT | NT | NT | 25.522.15 (3 of 3) | NT |

Example 4: Molecular Beacon Detection

To provide an additional level of direct sequence-based detection of amplified product (as opposed to indirect dye detection), molecular beacons, MB1 to MB4 (SEQ ID NOs: 73-76, respectively) targeting unique nucleotides within the *N. gonorrhoeae* amplicon of primer sets with promising Tp's combined with sensitivity, were designed and utilized for detection of amplification from nucleic acid extracted from live bacteria (Table 5). The molecular beacon probe was designed with 5' fluorophore/3' quencher modifications (6-Carboxyfluorescein (FAM)) and Black Hole Quencher 1 (BHQ1) included to provide target-specific fluorescent detection.

TABLE 5

Probe Sequences

| ID | Fluor | Quench | Sequence (5' to 3') | Sequence ID |
|---|---|---|---|---|
| MB1 | FAM | BHQ1 | CCGCAACGTGCCGCCGATGTTGCGG | SEQ ID NO: 73 |
| MB2 | FAM | BHQ1 | GCGTGACGGACGTGCCGCCGAT GTCACGC | SEQ ID NO: 74 |
| MB3 | FAM | BHQ1 | CGTTGGGACGGACGTGCCGCCAACG | SEQ ID NO: 75 |
| MB4 | FAM | BHQ1 | CGGGGACGGACGTGCCGCCGAT GTCCCCG | SEQ ID NO: 76 |

10-25 μl total volume reactions were evaluated utilizing eluate from 5 to 5×10³ CFU/mL extractions of *N. gonorrhoeae* as template input according to the methods described in Example 1. While use of a Molecular Beacon for detection resulted in a slight increase in reaction Tp, the ability to directly detect amplification products based on sequence, and thereby distinguish closely related species, is a desirable result.

TABLE 6

Time to Positive Cross-Reactivity (Probe Detection)

| Primers | Beacon | 5 × 10³ CFU/mL | 5 CFU/mL | NL | NS | NM | NC | NU | NTC |
|---|---|---|---|---|---|---|---|---|---|
| Set-13 | MB1 | 9.49 | 13.61 | No Amp | No Amp | No Amp | No Amp | No Amp | No Amp |
| Set-13 | MB2 | 8.42 | 12.01 | NT | NT | NT | NT | NT | No Amp |
| Set-13 | MB3 | 8.82 ± 0.71 | 12.54 ± 0.81 | No Amp | No Amp | No Amp | 19.8 | No Amp | No Amp |
| Set-13 | MB4 | 8.25 ± 0.89 | 11.72 ± 0.60 | No Amp | No Amp | No Amp | 22.01 | No Amp | No Amp |
| Set-14 | MB1 | 10.55 ± 0.03 | 14.47 ± 0.39 | No Amp | No Amp | No Amp | 21.32 | No Amp | No Amp |

TABLE 6-continued

Time to Positive Cross-Reactivity (Probe Detection)

| Primers | Beacon | 5 × 10³ CFU/mL | 5 CFU/mL | NL | NS | NM | NC | NU | NTC |
|---|---|---|---|---|---|---|---|---|---|
| Set-14 | MB2 | 12.44 ± 0.04 | 16.94 ± 0.11 | No Amp | No Amp | No Amp | 25.14 | No Amp | No Amp |
| Set-14 | MB3 | 10.95 ± 0.16 | 14.71 | No Amp | No Amp | No Amp | 23.04 | No Amp | No Amp |
| Set-14 | MB4 | 11.15 ± 0.06 | 14.94 ± 0.03 | No Amp | No Amp | No Amp | 24.01 | No Amp | No Amp |
| Set-15 | MB1 | 4.74 ± 0.60 | 7.76 ± 0.73 | No Amp | No Amp | No Amp | 18.16 | 13.48 | No Amp |
| Set-15 | MB2 | 8.09 ± 0.06 | 11.26 ± 0.11 | No Amp | No Amp | No Amp | 31.33 | No Amp | No Amp |
| Set-15 | MB3 | 7.43 ± 0.12 | 10.18 ± 0.47 | No Amp | No Amp | No Amp | 24.17 | 32.86 | No Amp |
| Set-15 | MB4 | 7.97 ± 0.13 | 10.4 ± 0.10 | 35.23 | No Amp | No Amp | 27.53 | No Amp | No Amp |

25 μl total volume reactions were prepared with eluate from extraction for 3 CFU/mL of *Neisseria gonorrhoeae* as template input. Reactions were performed according to the methods described in Example 1.

TABLE 7

Time to Positive (Probe Detection)

| Primers | Beacon | 3 CFU/mL | Freq. of Positive | NTC |
|---|---|---|---|---|
| Set-13 | SEQ ID NO: 75 | 18.76 ± 2.34 | 67% | No Amp |
| Set-15 | SEQ ID NO: 75 | 18.28 ± 0.21 | 67% | No Amp |

Although the foregoing invention has been described in some detail by way of illustration and example for purposes of clarity of understanding, it is readily apparent to those of ordinary skill in the art in light of the teachings of this invention that certain changes and modifications can be made thereto without departing from the spirit or scope of the appended claims. It is also to be understood that the terminology used herein is for the purpose of describing particular embodiments only, and is not intended to be limiting, since the scope of the present invention will be limited only by the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

We claim:

1. A composition comprising a sequence-specific primer set selected from the group consisting of Set-1 through Set-15.

2. The composition of claim 1, wherein the sequence-specific primer set is selected from the group consisting of: Set-5, Set-11, Set-13, Set-14 and Set-15.

3. The method of claim 2, wherein the sequence-specific primer set is Set-15.

4. The composition of claim 1, further comprising a probe.

5. The composition of claim 4, wherein the probe comprises a label.

6. The composition of claim 5, wherein the probe is a labeled polynucleotide.

7. The composition of claim 6, wherein the labeled polynucleotide comprises a sequence selected from the group consisting of: nucleotides 6-22 of SEQ ID NO: 73, nucleotides 5-24—of SEQ ID NO: 74, nucleotides 3-21 of SEQ ID NO: 75, and nucleotides 3-24 of SEQ ID NO: 76.

8. The composition of claim 6, wherein the labeled polynucleotide comprises a sequence selected from the group consisting of SEQ ID NO: 73 through SEQ ID NO: 76.

9. The composition of claim 6, wherein the label is a fluorophore.

10. The composition of claim 9, wherein the fluorophore is covalently attached to a terminus of the polynucleotide.

11. The composition of claim 4, wherein the probe is a molecular beacon comprising a fluorophore, a quencher, and a polynucleotide.

12. The composition of claim 11, wherein the molecular beacon comprises a sequence selected from the group consisting of SEQ ID NO: 73 through SEQ ID NO: 76.

13. The composition of claim 12, wherein the polynucleotide sequence consists of SEQ ID NO: 75.

14. A method of detecting *Neisseria gonorrhoeae* in a test sample, the method comprising:
    extracting nucleic acid from the test sample;
    amplifying a target sequence by reacting the nucleic acid extracted in step (a) with a reaction mixture comprising a strand displacement DNA polymerase and a sequence-specific primer set, wherein said sequence-specific primer set is selected from the group consisting of Set-1 through Set-15; and
    detecting the presence or absence of an amplified product of step (b), wherein the presence of said amplification product is indicative of the presence of *Neisseria Gonorrhoeae* in the test sample.

15. The method of claim 14, wherein the amplification step is performed for less than 15 minutes.

16. The method of claim 14, wherein the amplification step is performed for less than ten minutes.

17. The method of claim 14, wherein the reaction mixture further comprises a reverse transcriptase.

18. The method of claim 14, wherein detecting the presence or absence of the amplification product comprises hybridizing the amplified product with a probe comprising a polynucleotide attached to a label.

19. The method of claim 18, wherein the labeled polynucleotide comprises a sequence selected from the group consisting of: nucleotides 6-22 of SEQ ID NO: 73, nucleotides 5-24—of SEQ ID NO: 74, nucleotides 3-21 of SEQ ID NO: 75, and nucleotides 3-24 of SEQ ID NO: 76.

20. The method of claim 19, wherein the labeled polynucleotide comprises a sequence selected from the group consisting of: SEQ ID NO: 73 through SEQ ID NO: 76.

21. The method of claim 14, wherein the sequence-specific primer set is selected from the group consisting of: Set-5, Set-11, Set-13, Set-14 and Set-15.

22. The method of claim 21, wherein the sequence-specific primer set is Set-15.

23. The method of claim 14, wherein *Neisseria Gonorrhoeae* is present in the test sample at a concentration of ≤100 CFU/mL.

24. The method of claim 23, wherein *Neisseria Gonorrhoeae* is present in a test sample at a concentration of ≤10 CFU/mL.

25. The method of claim 24, wherein *Neisseria Gonorrhoeae* is present in the test sample at a concentration of ≤10 CFU/mL and the amplification reaction is performed for less than 15 minutes.

26. A kit comprising a composition according to claim 1, wherein said kit comprises a strand displacement polymerase.

27. The kit of claim 26, further comprising a reverse transcriptase.

* * * * *

UNITED STATES PATENT AND TRADEMARK OFFICE
CERTIFICATE OF CORRECTION

| | |
|---|---|
| PATENT NO. | : 10,954,572 B2 |
| APPLICATION NO. | : 16/719744 |
| DATED | : March 23, 2021 |
| INVENTOR(S) | : Andrea C. Dedent et al. |

It is certified that error appears in the above-identified patent and that said Letters Patent is hereby corrected as shown below:

In the Claims

Claim 3, Column 43, Line 8, reads "3. The method of claim ...." which should be deleted and replaced with "3. The composition of claim ...."

Signed and Sealed this
Thirteenth Day of December, 2022

Katherine Kelly Vidal
*Director of the United States Patent and Trademark Office*